United States Patent
Dudkiewicz et al.

(10) Patent No.: US 9,839,554 B2
(45) Date of Patent: Dec. 12, 2017

(54) LOWER BACK PAIN TREATMENT AND SPINAL PROTECTION DEVICE

(71) Applicants: Rosalie Dudkiewicz, West Orange, NJ (US); Dariusz Dudkiewicz, West Orange, NJ (US)

(72) Inventors: Rosalie Dudkiewicz, West Orange, NJ (US); Dariusz Dudkiewicz, West Orange, NJ (US)

( * ) Notice: Subject to any disclaimer, the term of this patent is extended or adjusted under 35 U.S.C. 154(b) by 281 days.

(21) Appl. No.: 14/615,841

(22) Filed: Feb. 6, 2015

(65) Prior Publication Data

US 2015/0342774 A1    Dec. 3, 2015

Related U.S. Application Data

(60) Provisional application No. 62/122,467, filed on Oct. 22, 2014.

(51) Int. Cl.
    *A61F 5/02*    (2006.01)
(52) U.S. Cl.
    CPC .................................. *A61F 5/028* (2013.01)
(58) Field of Classification Search
    CPC .......... A61F 5/028; A61F 5/024; A61F 5/026; A61F 5/03; A61F 13/14; A41F 11/16; A41F 9/002; A41F 9/005; A41F 9/02; A41D 1/20
    See application file for complete search history.

(56) References Cited

U.S. PATENT DOCUMENTS

| 5,038,760 | A | * | 8/1991 | Osborn ................... A61F 5/028 |
| | | | | 2/44 |
| 5,334,134 | A | | 8/1994 | Saunders |
| 5,399,150 | A | | 3/1995 | Saunders |
| 5,405,313 | A | | 4/1995 | Albin |
| 5,651,763 | A | | 7/1997 | Gates |
| 5,768,717 | A | * | 6/1998 | Le Sueur ........... A41D 13/0531 |
| | | | | 2/455 |
| 8,012,113 | B2 | | 9/2011 | Lee et al. |
| 8,226,587 | B2 | | 7/2012 | Segal et al. |
| 2004/0077981 | A1 | * | 4/2004 | Weaver, II ............... A61F 5/028 |
| | | | | 602/19 |
| 2007/0021706 | A1 | * | 1/2007 | Braunstein ............ A61F 5/0109 |
| | | | | 602/63 |
| 2010/0168630 | A1 | | 7/2010 | Cropper et al. |
| 2013/0090585 | A1 | | 4/2013 | Bue, Jr. et al. |

FOREIGN PATENT DOCUMENTS

| EP | 1452155 A2 | 2/2004 |
| WO | 2007027573 A2 | 3/2007 |

* cited by examiner

*Primary Examiner* — Ophelia A Hawthorne
(74) *Attorney, Agent, or Firm* — Gearhart Law LLC

(57) ABSTRACT

The present disclosure provides for a low back pain solution device design for individuals with acute or chronic lower back pain, individuals who are post-spinal surgery, or individuals who are pregnant and are experiencing low back pain or back injury. The device allows a user to continuously wear something that is both comfortable and discrete. The device accomplishes this task by flanking a user's lumbar and erector spinae muscles with soft yet firm cushions. This protects a user's lower spine processes and their peripheral nerves from be touched by any object that has the potential to compress it during sitting, sleeping or driving.

20 Claims, 20 Drawing Sheets

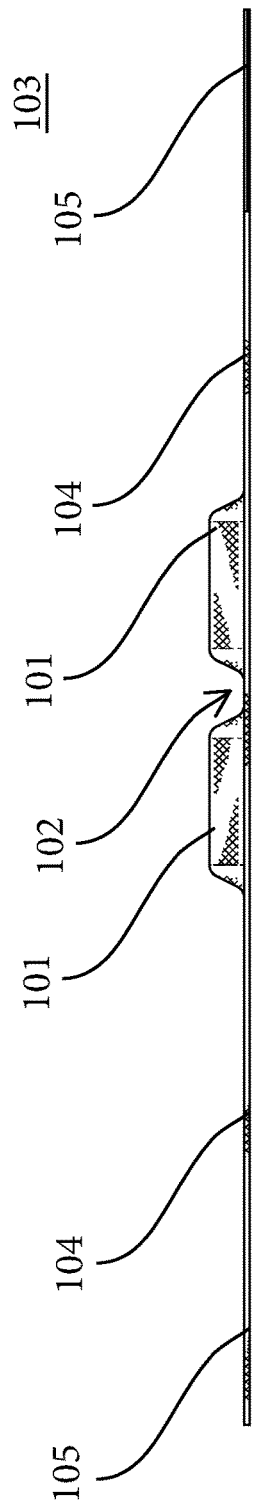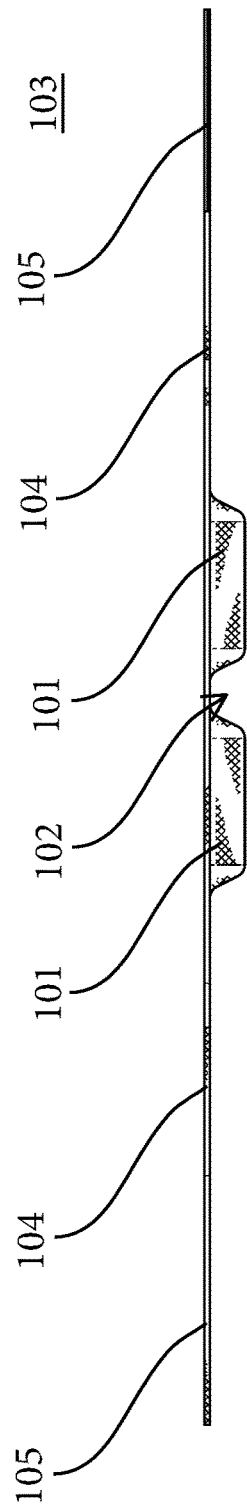

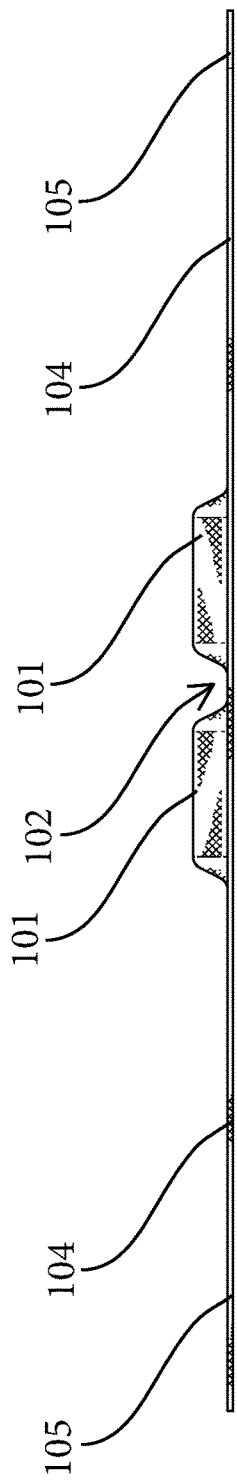
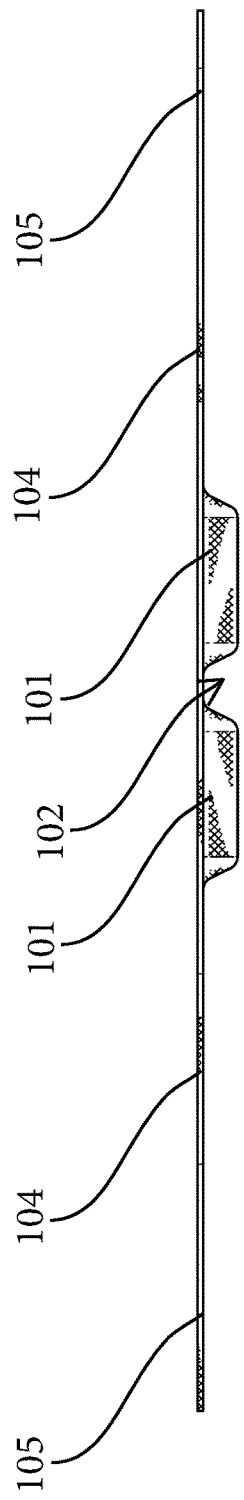

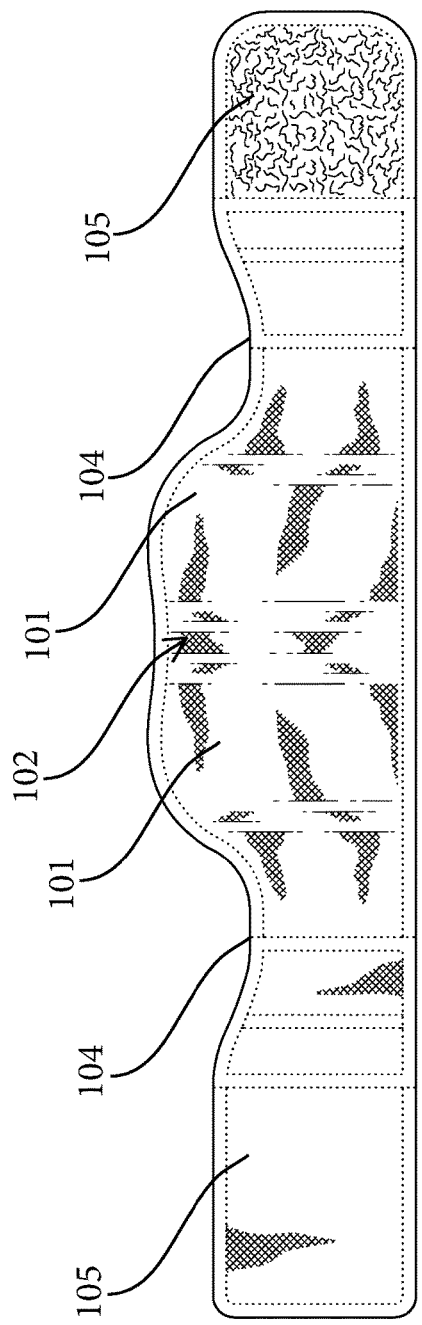
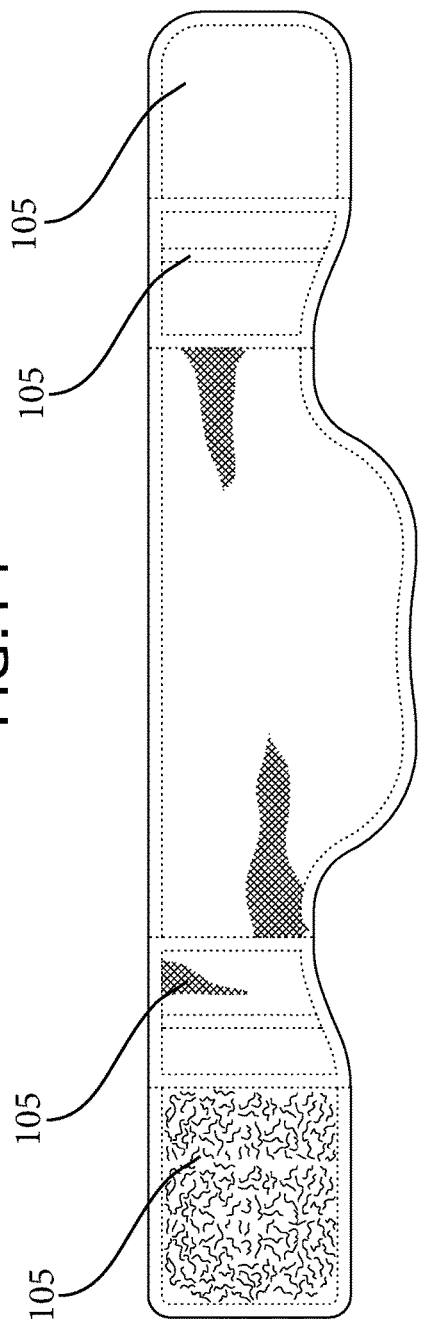
FIG. 14
FIG. 15

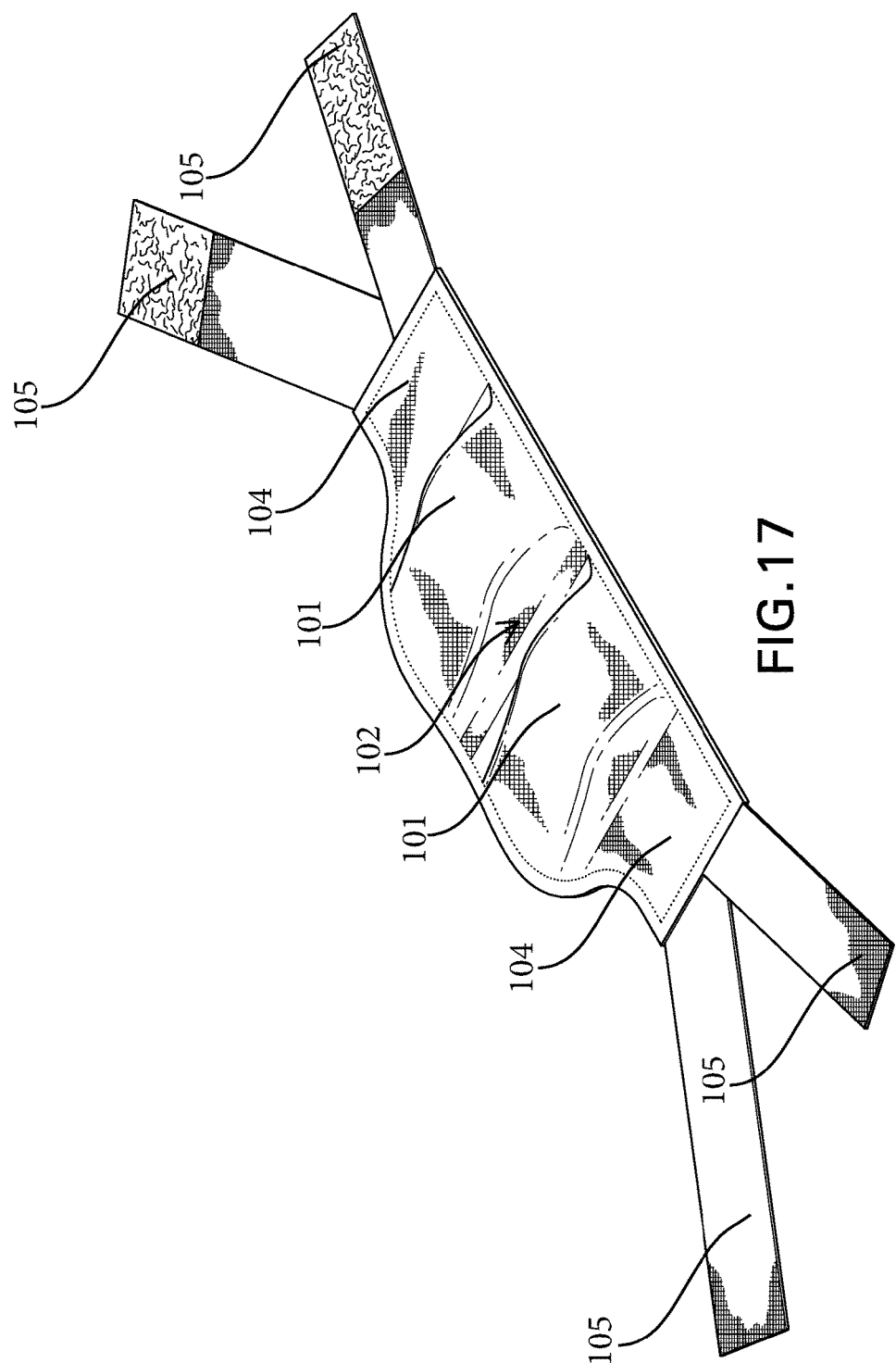

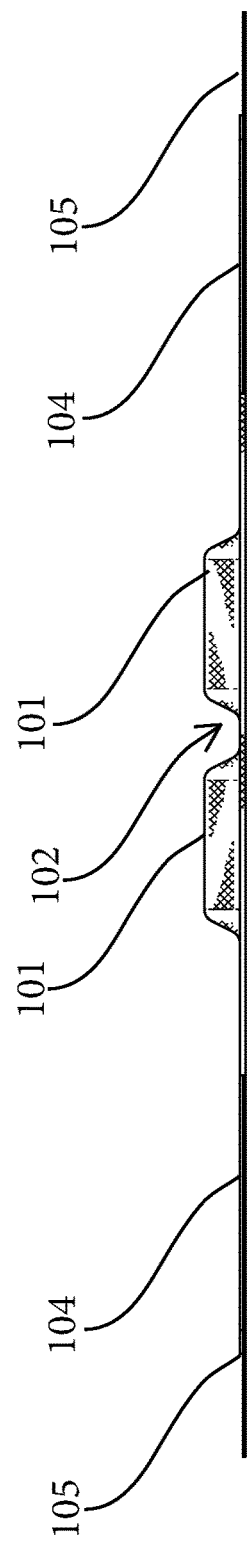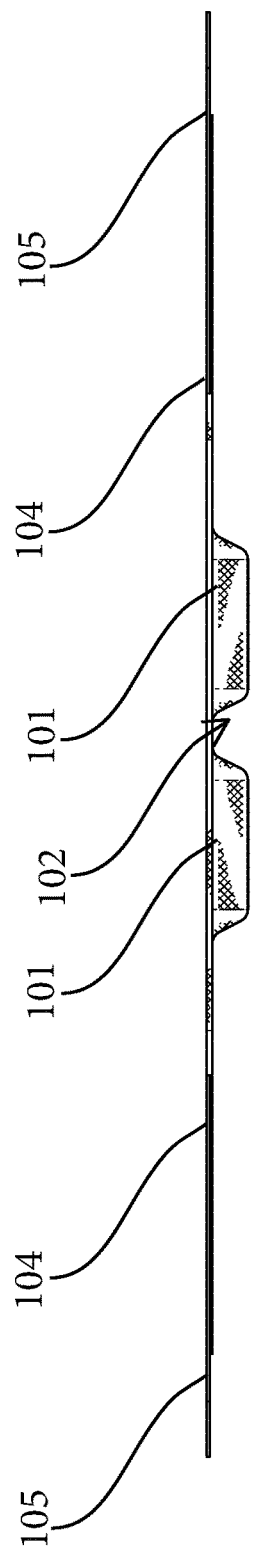

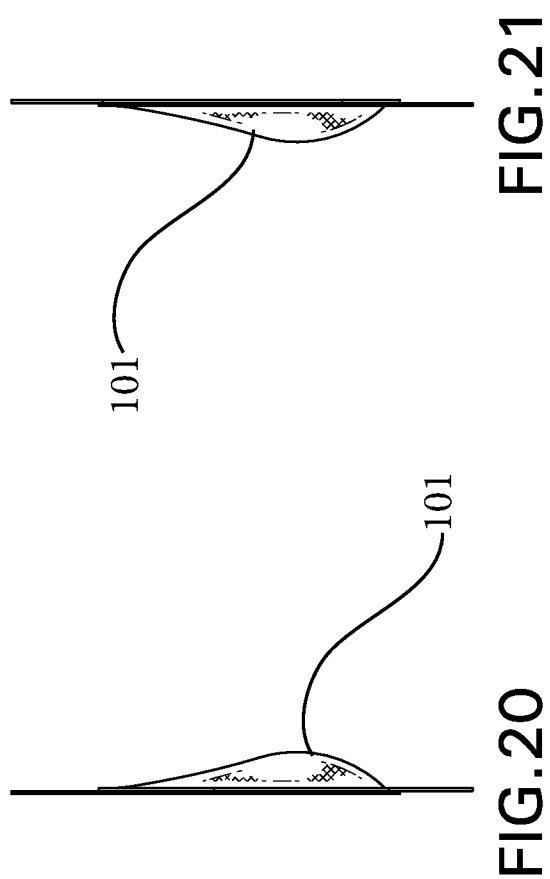

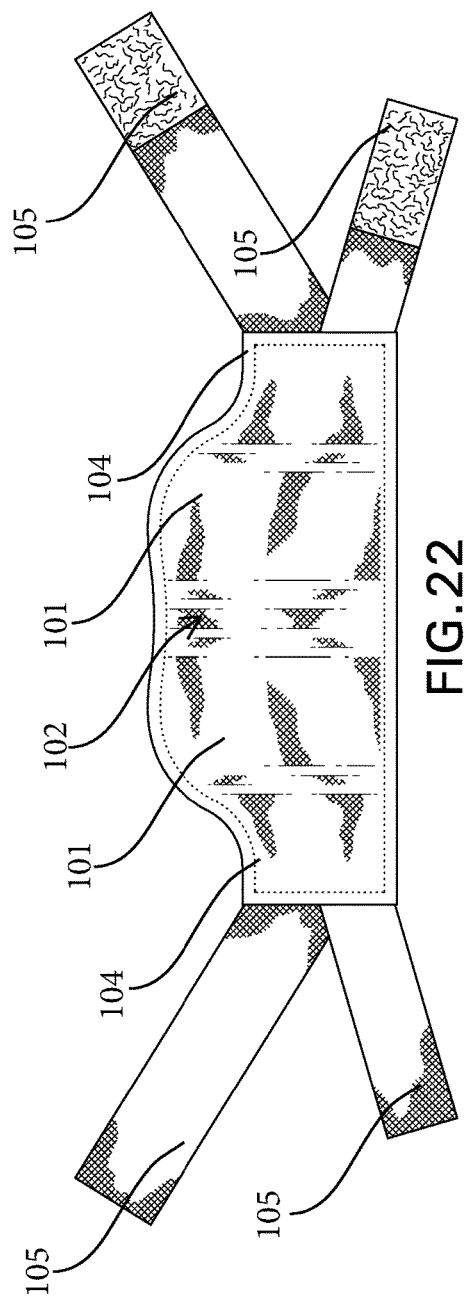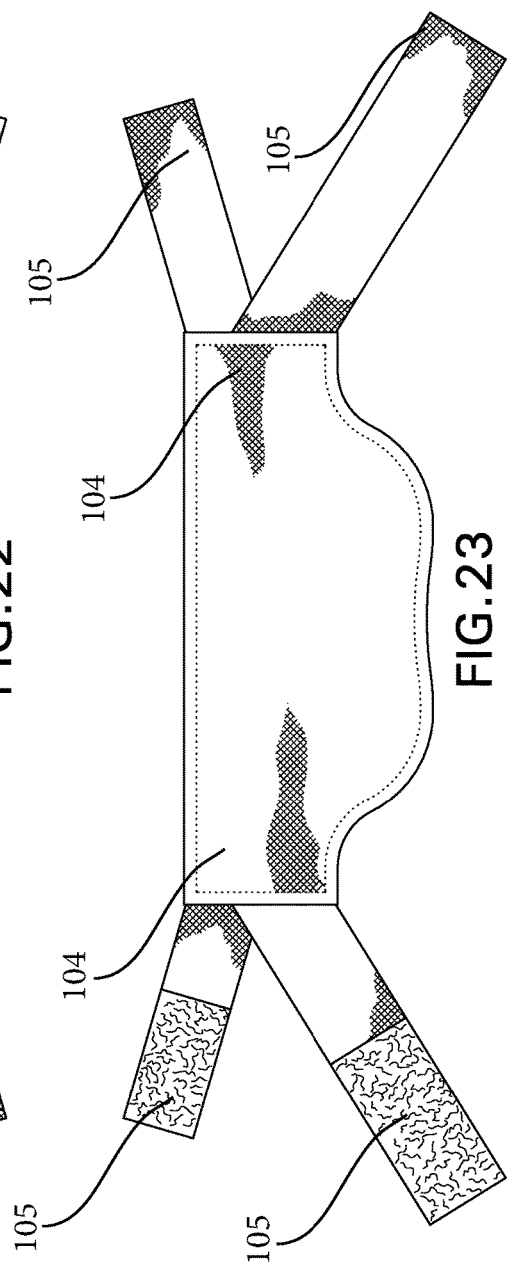

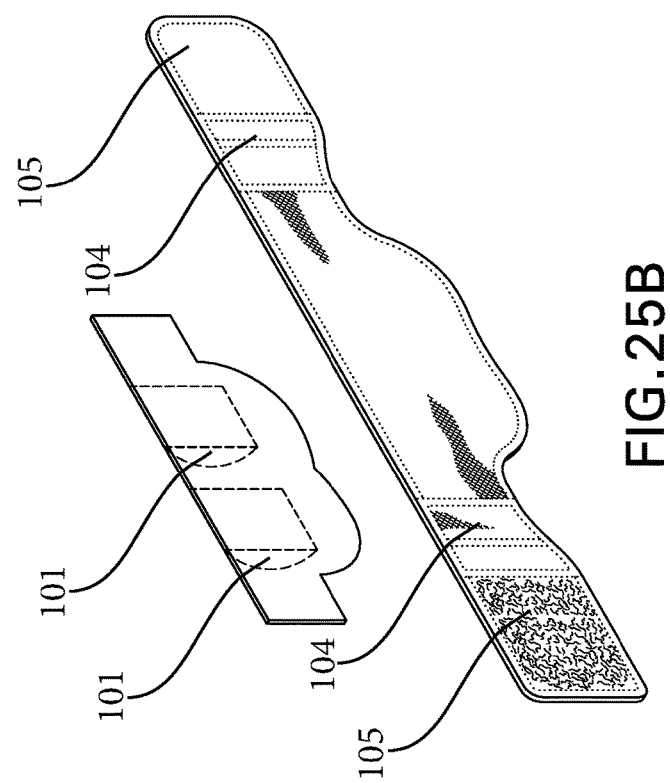
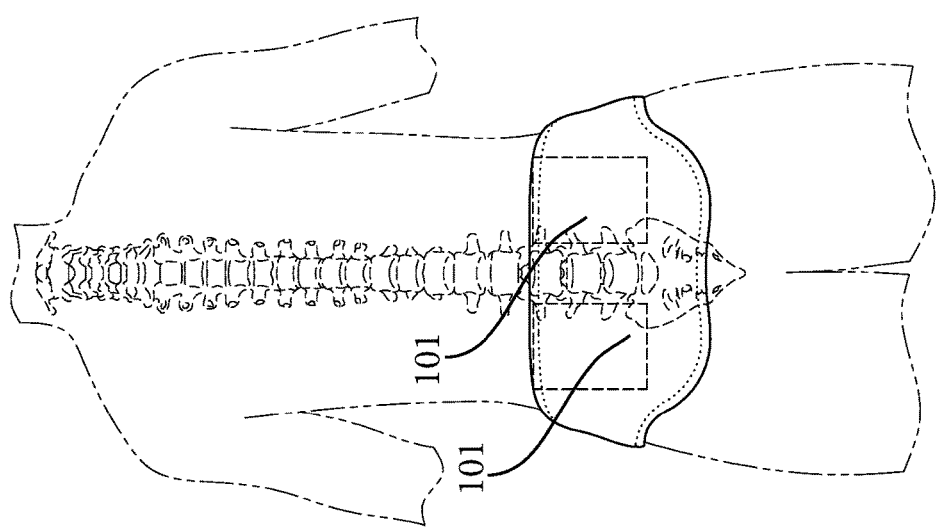
FIG. 25B
FIG. 25A

LOWER BACK PAIN TREATMENT AND SPINAL PROTECTION DEVICE

CLAIM OF PRIORITY

This application is a non-provisional application and claims priority to U.S. Provisional Patent Application No. 62/122,467 having a priority date of Oct. 22, 2014, the contents of which are hereby incorporated by reference.

FIELD OF THE EMBODIMENTS

The invention and its embodiments relate to medical devices, namely a device that is capable of alleviating lower back pain. In particular, the present invention and its embodiments relate to a device that prevents the lumbar spine process and its peripheral nerves from being touched or compressed.

BACKGROUND OF THE EMBODIMENTS

There are about 150-200 million adults that suffer from low back pain in United States, and it is the second most common reason people seek a doctor. This health problem results in about 2.4 million Americans chronically disabled and temporarily on disability. Lower back pain affects the spine's stability, flexibility, and strength as result cause pain, discomfort and stiffness during daily living activities such as sitting, driving or sleeping. A great majority of back pain experienced by the general population occurs in the lower portion of the back generally referred to as the lumbar area or the spinal segments L-3 through S-1 specifically. In order to comprehend the most causes of low back pain, it is essential to understand the functioning of the spinal column. The purpose of the human spinal column is to support and protects the body. The most common area of low back pain is at the spinal process segment L-3 to S-1. The spine process is composed of twenty four individual vertebrae. Each vertebra is attached and support by cartilages, muscles and ligaments to allow flexibility to bend over, and to rotate the torso. Each vertebra is connected by an intervertebral disc that functioning to provide cushion, and prevent compression to the peripheral spinal nerves. Whenever there is a shift of the vertebrae from its normal position caused by herniated discs, spinal stenosis, fractures, osteoarthritis or injury, it presses against the spinal nerves, and as a result it stimulates pain during daily living activities such as a sitting, sleeping, driving or bending. Likewise, low pain back is also caused by, the shifting of the 2 vertebrae caused by unequal pressure of the muscles supporting the spine column. This can occur due to overuse or injury of the muscles or ligaments, uneven muscular stress, emotional tension. The majority of low back pain is managed with conservative treatment such as rest, analgesic, anti-inflammatory medications in conjunction with physical therapy to strength the back muscles to support the spine column to relief pain or eliminate it. Another conventional treatment used to address back pain due to injury or non-injury is applying pressure to the area with orthopedic belt devices.

Review of Related Technology:

U.S. Pat. No. 8,226,587 pertains to a spinal support and brace device configured to support the lower back and that anchors on portion for the pelvis and are configured to support and align one or more lumber vertebrae.

International Patent Application No.: WO2007027573 pertains to a lumbar lordosis correction brace comprised of a lower portion, adapted to be comfortably affixed to the lower truck of a patient, and upper portion, adapted for comfortably encircling the upper trunk of a patient such that the two portions work together to provide uniform pressure against a patient's spine. This patent application also provides for the ability to displace, in a controlled manner, to provide additional support of the lumbar.

U.S. Pat. No. 5,405,313 pertains to an adjustable back support comprising a pelvic girdle that has been adapted to fit snugly around a user's waist, a pair of hip crutches adapted to be vertically disposed on each side of a user's body, wherein each hip crutch extends upwardly at a small forward angle between the pelvic girdle and the corresponding armpit.

U.S. Patent Publication No.: 2010/0168630 pertains to a rigid lumbar compression piece, that includes first and second, separate, opposing and mating front attachment panels; and a separate, laterally adjustable, rigid lumbar compression piece configured for positioning only at the rear of a wearer, wherein pulling of a cord causes the brace both circumferentially to tighten and to concentrate compression and pressure of the separate, laterally adjustable, rigid lumbar compression piece pushed directly against a spinal region of a wearer's back with the aid of a number of apertures through which the cord or cords pass.

U.S. Patent Publication No.: 2013/0090585 pertains to a neuromuscular training device for enhancing the alignment of the upper torso of a user. The device is preferably configured specifically to provide scapula retraction and stabilization while providing stated and dynamic neuromuscular training.

U.S. Pat. No. 5,334,134 pertains to a lumbosacral back support member which is releasably secured to the user by a stabilizing belt. Generally, this device is used over a user's clothes. This stabilizing belt may be inserted into the belt loops of a user's pants, attached to these belt loops, or engaged within the narrow portions of the user's waist.

U.S. Pat. No. 5,399,150 pertains to a lumbosacral back support system with interchangeably and postionally-adjustable lumbosacral orthopedic support members for supporting the spine of a user during physical activity, athletics activities, or for use by industrial workers.

U.S. Pat. No. 8,012,113 pertains to a spinal brace that includes a flexible air injectable band configured to be disposed about a torso of a user and to provide traction to a spine of the user. The device also comprises at least one support panel configured to provide support by compression to at least one region of a user's torso.

U.S. Patent Publication No.: 2014/0221892 pertains to a maternity support belt that includes a curved support edge which matches the female pelvic curve, to support a gravid abdomen. The maternity belt includes a lumbosacral supporting section that applies a compressive force against the lumbosacral portion of the wearer's back, and a pair of gravid abdominal support sections on opposite lateral sides of the lumbosacral supporting section and contiguous thereto. The gravid abdominal support sections adjustably overlap and connect to each other on the wearer's front side.

U.S. Design Pat. No. D657063 pertains to a back support.

Various devices are known in the art. However, their structure and means of operation are substantially different from the present invention. Such devices fail to provide a device that can be easily operated through medical gloves and that provide a tool that can be used on a wider array of hemorrhoidal tissue. At least one embodiment of this invention is presented in the drawings below and will be described in more detail herein.

SUMMARY OF THE EMBODIMENTS

The present invention provides for a device, comprising: a back member having a front surface, a rear surface, a left side and a right side; at least two raised portions or protrusions said at least two raised protrusion being fixed to the front surface of said back member; and which create a cavity between said at least two raised protrusions for receiving a spinal column of an individual; a first extension piece, attached to said left side of said back member; a second extension piece, attached to said right said of said back member; and a mechanism for attaching said first extension piece to said second extension piece. The at least two raised portions or protrusions can be comprised from any material selected from the group of cushion, rubber, foam, wool, feathers, hair, or paper.

The present invention is a device to help individuals suffering from acute or chronic lower back pain to perform their daily living activities such as sitting, sleeping or driving without or with less pain. The invention also allows individuals recovering from back surgery or back injury to recovery fast. It accomplishes it by the following: It protects the incision site (stitches) at the spine from been compressed and contact with any object during sitting (chair or sofa) or sleeping (mattress), driving or riding in a car; air can flow freely to the surgical site, as a result promote healing; the individual is able to sit or lie down in a back resting position without having pressure against the incision site. In another embodiment of the invention, the cushion pads may be carved lateral to the spine to accommodate rods or others device placed in the back during back surgery. This feature prevents the rods or devices from being compressed during sleeping/sitting or driving which can be uncomfortable to the wearer. In addition, the device can be continuing used for long period of time post-surgery in people who has to return to work and they perform desk work such as secretary or job as truck driver. It also promotes good posture which in turn prevents future low back pain. The present invention's function is to reduce or eliminate pain by preventing the lumbar spine process and its peripheral nerves from being touched or compressed by any object during sitting, sleeping, or driving. The device accomplishes this by helping the erector spinae muscles to support the spine process to be in proper alignment, and by preventing the spine from touch any object that has potential to compress it, and stimulate pain. Another feature of the device is that the front embodiment spandex fabric gently compresses the abdominal cavity, and intra-abdominal pressure is increased, and as a result the lumbar is supported and corrected. This mechanism relief pain and promote proper posture. Moreover, it can be used comfortable 24/7 hours week discreet under the wearer garment. The inside back part is enclosed by an envelope case appropriate designed for female, male and pregnant woman. In addition, the Low Back Pain solution device has a tail end piece that fits well inside the user's underwear, and it is hidden well that only the individual knows that she/he is wearing it, as a result it ease the user's pain, without feeling embarrassed to use it. In general, the present invention succeeds in conferring the following, and other not mentioned, benefits and objectives.

It is an object of the present invention to provide a means for relieving back support.

It is an object of the present invention to provide a medical device.

It is an object of the present invention to provide a means for removing pressure from a user's lumbar.

It is an object of the present invention to provide a device that supports the erector spinae muscles.

It is an object of the present invention to provide a means for protecting surgical incisions along the spine.

BRIEF DESCRIPTION OF THE DRAWINGS

FIG. 2 is a front view of an embodiment of the present invention.

FIG. 3 is a rear view of an embodiment of the present invention.

FIG. 10 is a front view of an alternative embodiment of the present invention.

FIG. 11 is a rear view of an alternative embodiment of the present invention.

FIG. 14 is a top view of an alternative embodiment of the present invention.

FIG. 15 is a bottom view of alternative embodiment of the present invention.

FIG. 17 is a front perspective view of another alternative embodiment of the present invention.

FIG. 18 is a front view of another alternative embodiment of the present invention.

FIG. 19 is a rear view of another alternative embodiment of the present invention.

FIG. 20 is a right side view of another alternative embodiment of the present invention.

FIG. 21 is a left side view of another alternative embodiment of the present invention.

FIG. 22 is a top view of another alternative embodiment of the present invention.

FIG. 23 is a bottom view of another alternative embodiment of the present invention.

FIG. 25a is a rear view of an embodiment of the present invention while in use.

FIG. 25b is a perspective view of an embodiment illustrating the rear cushion pads of the present invention.

DESCRIPTION OF THE PREFERRED EMBODIMENTS

Figure 1:
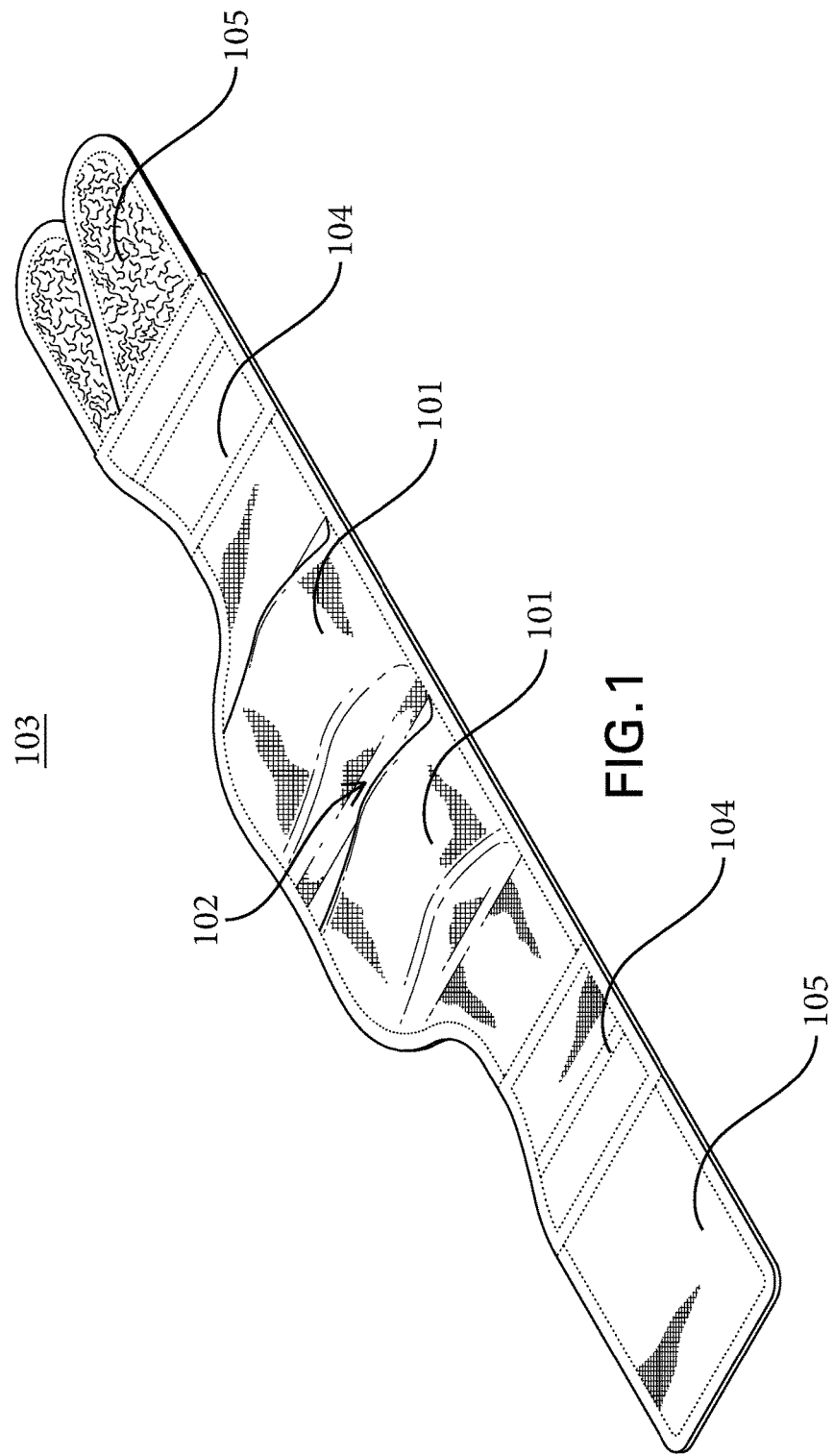
FIG. 1 is a front perspective view of an embodiment of the present invention.
Figures 4, 5:
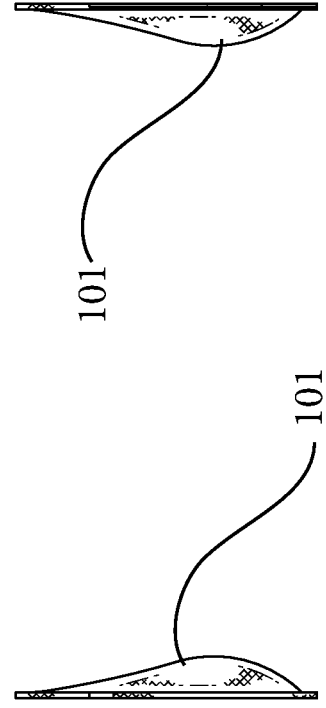
FIG. 4 is a right side view of an embodiment of the present invention.
FIG. 5 is a left side view of an embodiment of the present invention.
Figure 6:
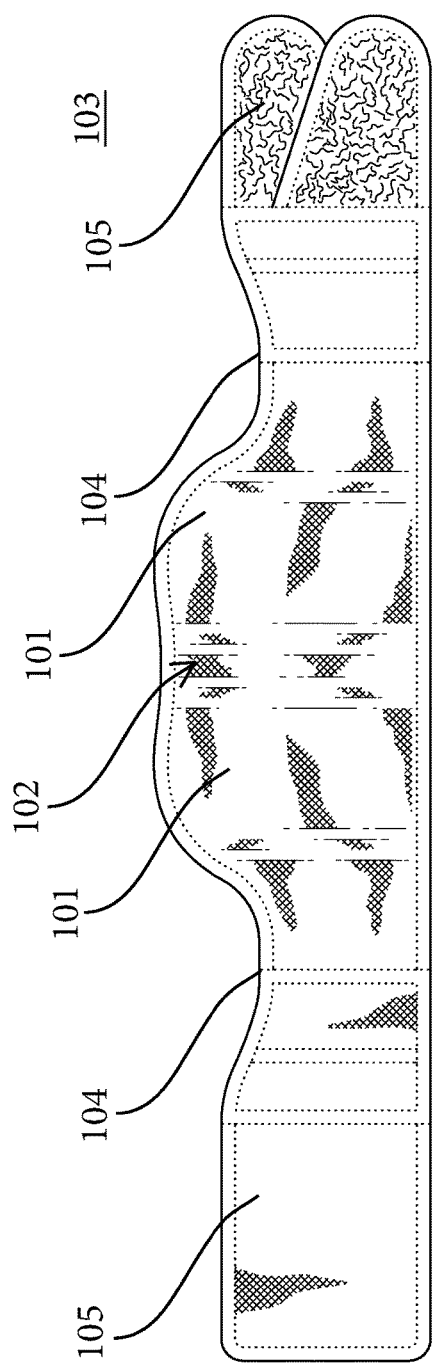
FIG. 6 is a top view of an embodiment of the present invention.
Figure 7:
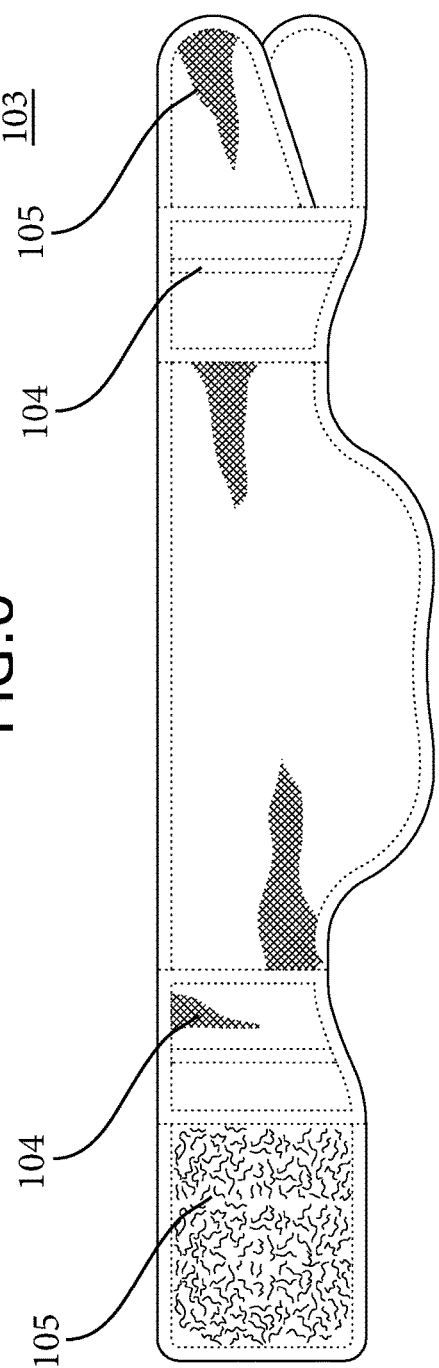
FIG. 7 is a bottom view of an embodiment of the present invention.

The preferred embodiments of the present invention will now be described with reference to the drawings. Identical elements in the various figures are identified with the same reference numerals.

Reference will now be made in detail to each embodiment of the present invention. Such embodiments are provided by way of explanation of the present invention, which is not intended to be limited thereto. In fact, those of ordinary skill in the art may appreciate upon reading the present specification and viewing the present drawings that various modifications and variations can be made thereto.

Low Back Pain solution device features two main components: the outside envelope and the back section. These components can be constructed from, by non-limiting example ethyl vinyl acetate (EVA) or nitrile butadiene rubber foam. In one embodiment, the back section is a single piece shaped similarly to a human buttocks. In a preferred embodiment, the back section features two cushion pads, as well as a cavity. Preferably, this cavity will be 6 centimeters wide. The purpose of this cavity is to protect the spinal column and peripheral nerves from being touched or compressed by any object. Objects that can frequently cause such touching or compression include chairs, sofas, beds or car seats. This function also prevents pressure against incision site of post-spine surgery individual or individual with injured back. It allows the individual to perform daily activities such as sleeping, sitting or driving.

Further, any spinal incision is protected from being touched by any object during the above activities, which makes a user's healing process fast and effective. In turn, this makes the recovery period shorter. Another significant feature of this device is the two soft yet firm cushioned pads. Preferably, these pads have rectangular base with a rounded top, however, this does not mean that other shapes would not be suitable. This rounded top lies on the erector spinae muscles allowing the spine process and its nerves to be free from contact due to any object. In a preferred embodiment, these pads are aligned parallel to a user's lower spine processes and erector spinae musculature. These pads hold the muscles in place to support the spine; allowing good blood flow to the area, and it prevents the muscles to fatigue, which also promotes healing.

The present invention also facilitates the correction of curvature and extension of a user's spine. This facilitation results in easing a user's back pain while helping them maintain proper posture. Additionally, the outside part has the purpose to enclose the back piece, as well it front is made of spandex material that helps support the abdominal muscles, a result promote proper posture and support the spine. In yet another preferred embodiment, the cavity has preferred dimensions of 7 cm wide while being and 2.5 cm deep, having a layer of 2.4 mm sheet of EVA and NBR foam. In one embodiment, the back section is enclosed by a comfortable non-spandex and washable fabric, but this should not be construed as the invention being limited to these fabrics.

In another embodiment, the present invention is equipped with a flap for providing privacy shaped to fit well under or over the wearer's underwear to keep the device secure in place. The present invention also includes two pieces of extension fabrics to provide a gently firm compression in the abdominal muscles to better fit and promote good posture.

Figure 8:
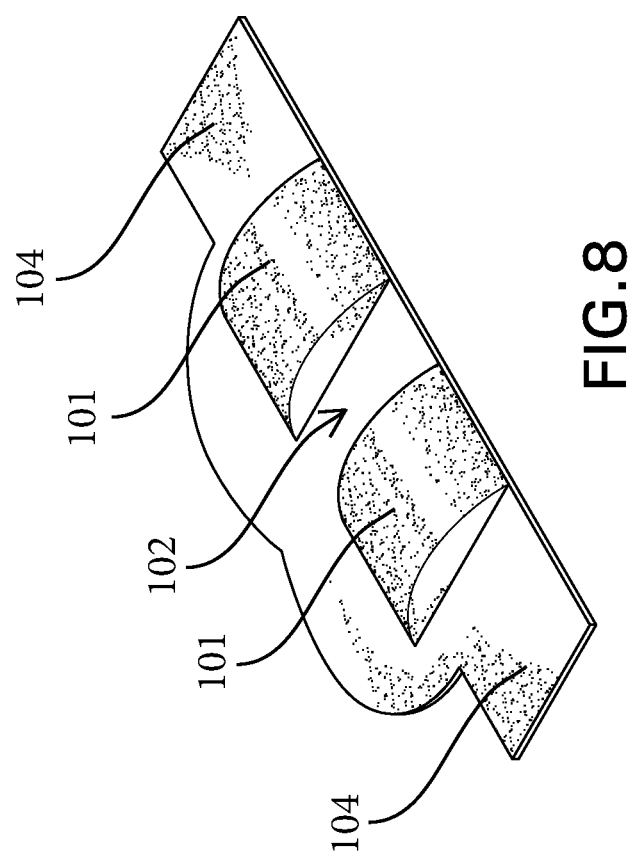
FIG. 8 is a front perspective view of a back member of an embodiment of the present invention.
Figure 9:
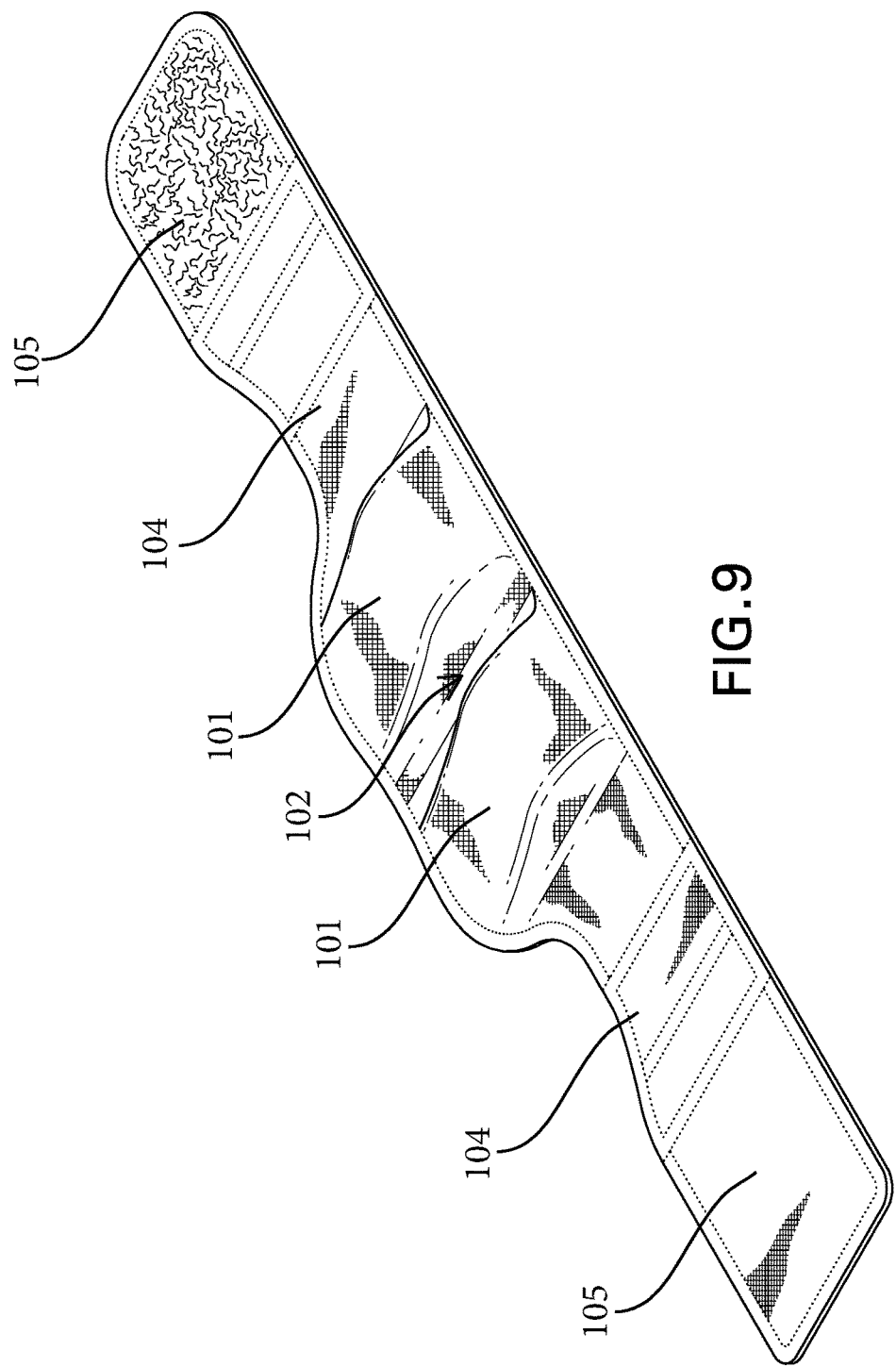
FIG. 9 is a front perspective view of an alternative embodiment of the present invention.
Figures 12, 13:
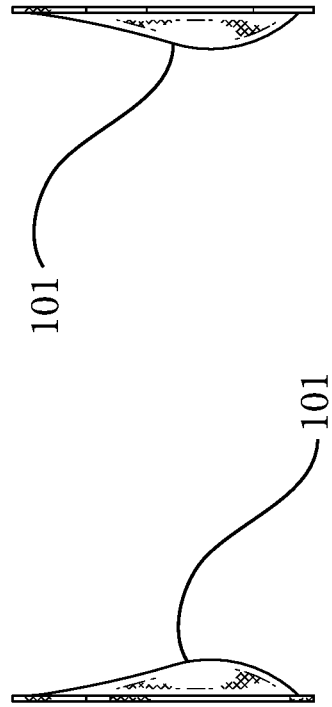
FIG. 12 is a right side view of an alternative embodiment of the present invention.
FIG. 13 is a left side view of an alternative embodiment of the present invention.
Figure 16:
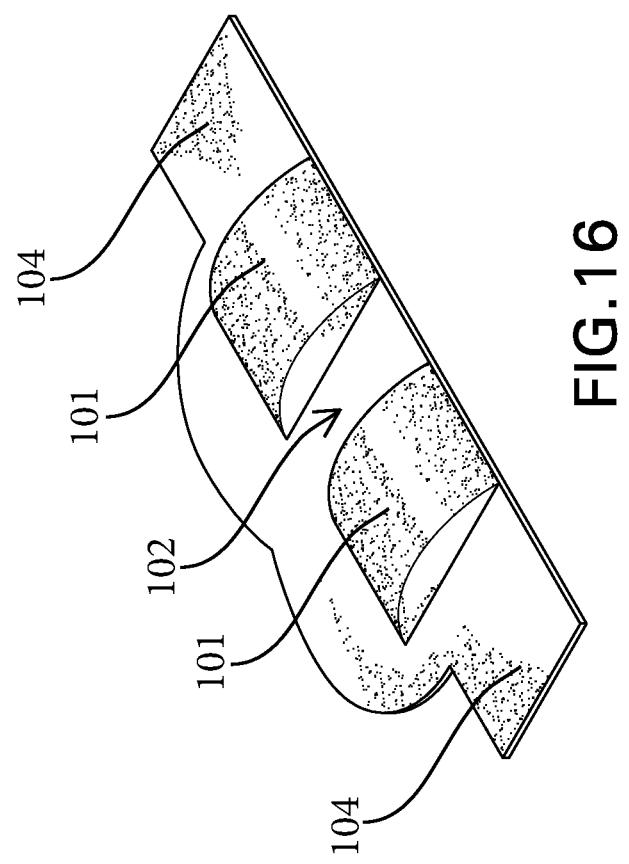
FIG. 16 is a front perspective view of a back member of an alternative embodiment of the present invention.

Referring to FIGS. 1-8, an embodiment of the present invention is detailed. Specifically, FIG. 1 shows back member 103, cushions 101, cavity 102, first and second extensions fabrics 104, and mechanism for attaching 105. In the depicted embodiment, the mechanism for attaching is one strap equipped with hoop fasteners and two straps equipped with loop fasteners. FIG. 8 depicts the back member.

Referring to FIGS. 9-15, an alternative embodiment of the present invention is shown. This embodiment is substantially similar to the one depicted in FIGS. 1-7, however, the mechanism for attaching 105 is different. This embodiment is provided to show that a number of different mechanisms for attaching are contemplated by the present disclosure. It should be noted that the back member of FIG. 15 is identical to the back member of FIG. 8.

Figure 24:
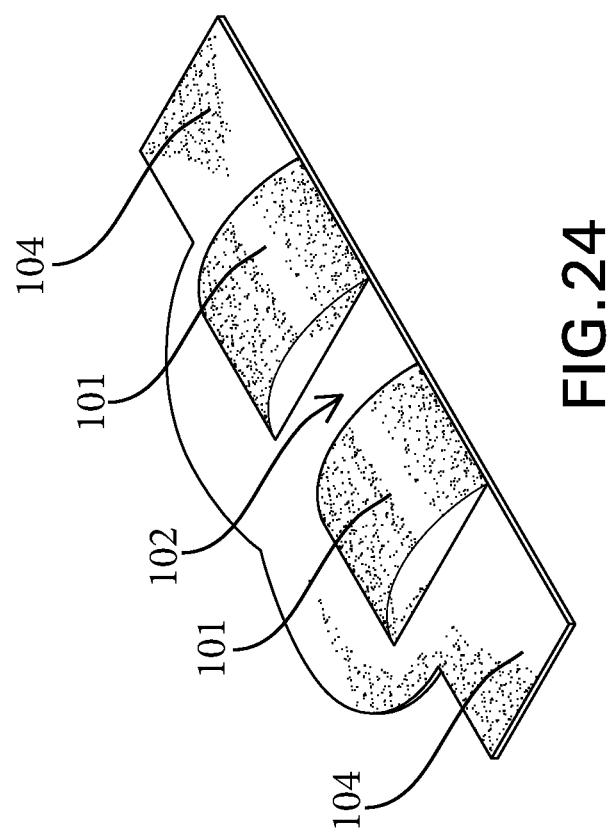
FIG. 24 is a front perspective view of a back member of another alternative embodiment of the present invention.
Figure 26:
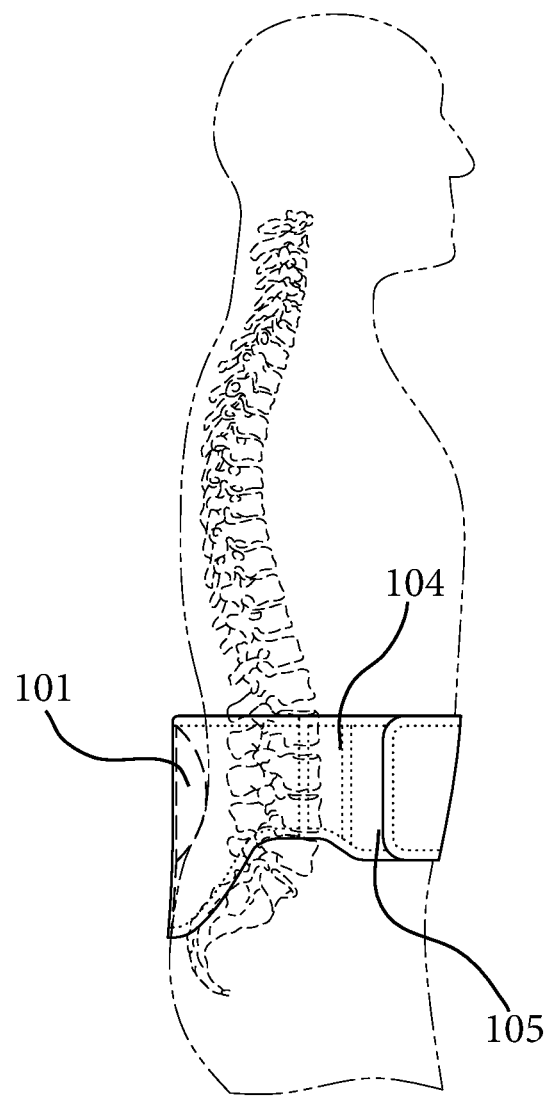
FIG. 26 is a right side view of an embodiment of the present invention while in use.
Figure 27:
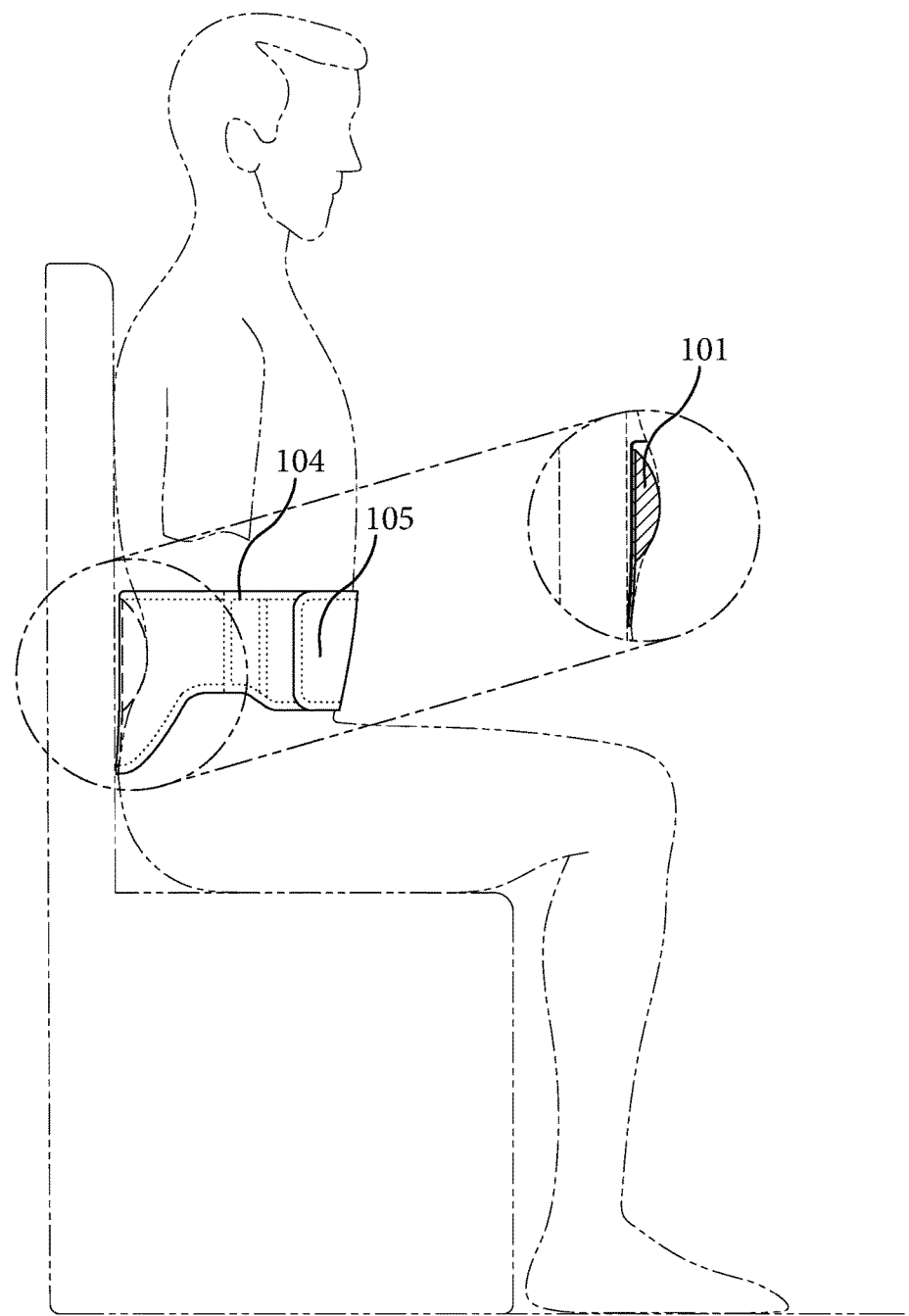
FIG. 27 is a right side view of an embodiment of the present invention while in use by a male who is sitting.

Referring to FIGS. 16-24, yet another alternative embodiment of the present invention is provided. FIG. 15 shows back member 103, cushions 101, cavity 102, and mechanism for attaching 105. Here, mechanism for attaching 105 takes the form of a plurality of elastic straps equipped with complimentary hook and loop fasteners. The embodiment of FIG. 15 is provided to show that the first and second extension fabrics located in the other depicted embodiments are optional. It should be noted that the back member of FIG. 24 is identical to the back members of FIGS. 8 and 16.

Referring to FIGS. 25a-27, various views of an embodiment of the present invention are provided. These views are provided to illustrate where the present invention is placed on a user while in use. Specifically, FIGS. 25a-27 highlight that a user's spine is positioned in the cavity of the present invention. This provide significant benefits to the user in that the position of the spine is secured and any incision that might exist along a user's spine will not be aggravated by the use of the present invention.

Figure 28:
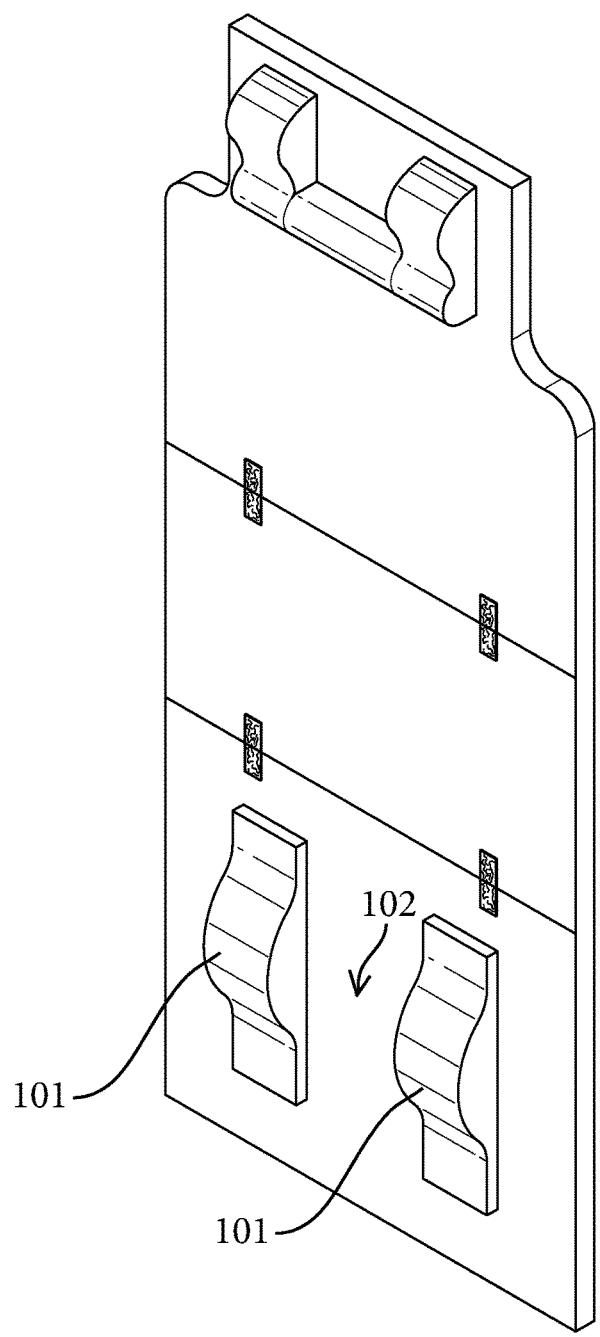
FIG. 28 is a perspective view of an alternative embodiment of the present invention.

In an alternative embodiment of the invention, as shown in FIG. 28, the invention may be adapted and configured to protect the user's lower spine and the user's spine at the rear and base of the neck. In this alternative embodiment, the invention may be unfolded into three separate pieces and placed over or attached to the back spine of a chair or seat where the user's lower spine may fit into the channel or cavity created by the protruding pads. In addition, the upper spine on the neck portion of a user may rest on the upper portion of the invention. In another embodiment of this invention, the full length of a user's spine is supported. In another embodiment, the channel where the user's spine is supported spans the entire length of the invention such that the user's entire spine fits into the cavity or channel of the apparatus. In another embodiment, the apparatus may be in one piece or be folded into 2 or more components.

Figure 29B:
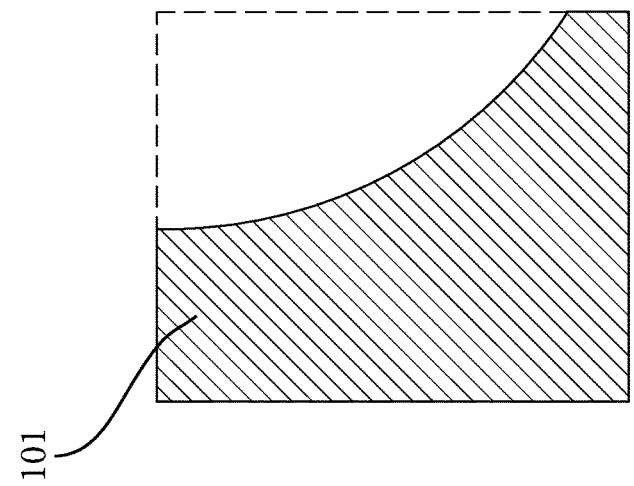
FIG. 29b is a sectional side view of the cushion pads of the present invention
Figure 29A:
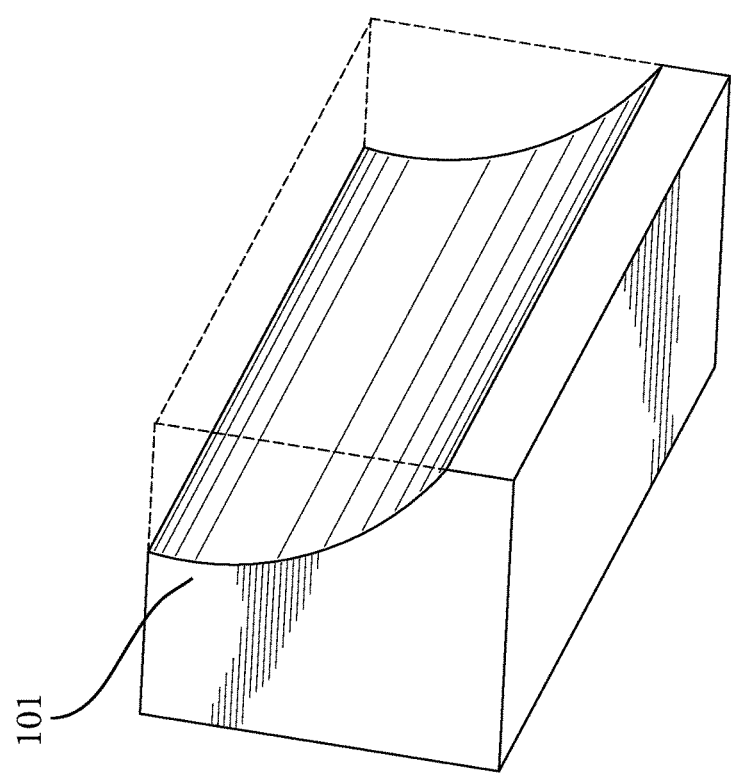
FIG. 29a is a perspective view of the cushion pads of the present invention.

In another embodiment of the present invention, the cushion pads can also be carved lateral to the spine to accommodate the rods or others devices placed in a user's back during surgery (as show in FIG. 29a and FIG. 29b). This feature prevents the rods or devices from being compressed during sleeping/sitting or driving, which can be uncomfortable to the user. In another embodiment of the present invention, the invention may be adapted and configured to support other bones of the body, including but not limited to supporting the bones of the arms and legs. In another embodiment of the present invention, the pads that create the channel or cavity where the user's spine fits into may be a unitary component. In another embodiment, the present invention may be worn as an outer garment such as a corset. In another embodiment, the present invention may be completely waterproof. In another embodiment, the interior pads may be removable, adjustable and detachable. In another embodiment of the invention, a user may insert the pads into the device and the pads are customizable and may be placed to fit any user's spine or measurements. In another embodiment, the pads can be of any material and of various thicknesses to confirm to a user's body. In another embodiment, the present invention may contain heating or cooling pads within the pads or within the channel or cavity.

When introducing elements of the present disclosure or the embodiment(s) thereof, the articles "a," "an," and "the" are intended to mean that there are one or more of the elements. Similarly, the adjective "another," when used to introduce an element, is intended to mean one or more elements. The terms "including" and "having" are intended to be inclusive such that there may be additional elements other than the listed elements.

While the disclosure refers to exemplary embodiments, it will be understood by those skilled in the art that various changes may be made and equivalents may be substituted for elements thereof without departing from the scope of the disclosure. In addition, many modifications will be appreciated by those skilled in the art to adapt a particular instrument, situation or material to the teachings of the disclosure without departing from the spirit thereof. Therefore, it is intended that the disclosure not be limited to the particular embodiments disclosed.

What is claimed is:

1. A device, comprising:
    a back member having a front surface, a rear surface, a left side and a right side;
    at least two raised portions or protrusions said at least two raised protrusion being fixed to the front surface of said back member; and which create a cavity between said at least two raised protrusions for receiving a spinal column of an individual,
        wherein the at least two raised portions and the cavity are configured to prevent compression of the spinal column;
    a first extension piece, attached to said left side of said back member;
    a second extension piece, attached to said right said of said back member; and
    a mechanism for attaching said first extension piece to said second extension piece.

2. The device of claim 1, wherein said at least two raised portions or protrusions are comprised of a material selected from the group of: cushion, rubber, foam, wool, feathers, hair, or paper.

3. The device of claim 1, wherein said first extension piece is comprised of fabric.

4. The device of claim 1, wherein said second extension piece is comprised of fabric.

5. The device of claim 1, further comprising a flap for providing privacy to the individual's backside.

6. The device of claim 1, wherein the at least two raised protrusions are configured to be a width and depth suitable to ensure that approximately no pressure is placed on a portion of the spinal column received within the cavity formed between the at least two raised protrusions.

7. The device of claim 1, wherein the at least two raised portions have a rectangle base with a round top.

8. The device of claim 1, wherein the at least two raised portions or protrusions are comprised of nitrile butadiene rubber foam and ethyl vinyl acetate foam.

9. The device of claim 1, wherein said mechanism for attaching is comprised of at least one strap equipped with loop fasteners and at least one strap equipped with hook fasteners.

10. The device of claim 1, wherein the mechanism for attaching is selected from the group of: hook and eye closures; buckles, buttons, back closures, shank strap, snap fasteners, zippers, sew-on snaps or snap buttons.

11. The device of claim 1, wherein the at least two raised portions are comprised of nitrile butadiene rubber foam and ethyl vinyl acetate foam.

12. The device of claim 1, wherein the back member is enclosed by a washable fabric.

13. The device of claim 1, wherein said mechanism for attaching is comprised of one strap equipped with a plurality of loop fasteners and two straps equipped with a plurality of hook fasteners.

14. The device of claim 1, wherein the front surface includes spandex and the rear surface is enclosed by a non-spandex and washable fabric.

15. A device, comprising:
    a back member having a front surface, a rear surface, a left side and a right side;
    at least two raised portions or protrusions said at least two raised protrusion being fixed to the front surface of said back member; and which create a cavity between said at least two raised protrusions for receiving a spinal column of an individual,
        wherein the at least two raised protrusions and the cavity are configured to prevent compression of the spinal column; and
    a mechanism for attaching.

16. The device of claim 15, wherein the mechanism for attaching is comprised of a first elastic band and a second elastic band;
    wherein said first elastic band is equipped with a plurality of hook fasteners; and
    wherein said second elastic band is equipped with a plurality of loop fasteners.

17. The device of claim 15, wherein the at least two raised protrusions are configured to be a width and depth suitable to ensure that approximately no pressure is placed on a portion of the spinal column received within the cavity formed between the at least two raised protrusions.

18. The device of claim 15, wherein the at least two raised portions or protrusions have a rectangle base with a round top.

19. The device of claim 15, wherein the at least two raised portions or protrusions are comprised of a material selected from the group of: cushion, rubber, foam, wool, feathers, hair, or paper.

20. The device of claim 15, wherein the at least two raised portions or protrusions are comprised of nitrile butadiene rubber foam and ethyl vinyl acetate foam.

* * * * *